(12) United States Patent
Zegdi et al.

(10) Patent No.: US 6,187,020 B1
(45) Date of Patent: Feb. 13, 2001

(54) CONNECTING DEVICE FOR ANASTOMOSIS, DEVICE FOR FITTING FASTENERS AND IMPLANT INCLUDING THEM

(75) Inventors: Rachid Zegdi, Clamart; Jean-Paul Gerardin, La Garenne Colombes; Eric Perouse, L'Isle Adam, all of (FR)

(73) Assignee: Laboratoire Perouse Implant, Bornel (FR)

( * ) Notice: Under 35 U.S.C. 154(b), the term of this patent shall be extended for 0 days.

(21) Appl. No.: 09/347,577

(22) Filed: Jul. 6, 1999

(51) Int. Cl.[7] .................................. A61B 17/08
(52) U.S. Cl. ............................ 606/153; 606/152
(58) Field of Search .................. 606/153–158, 606/151, 152

(56) References Cited

U.S. PATENT DOCUMENTS

| | | |
|---|---|---|
| 3,974,835 | 8/1976 | Hardy, Jr. . |
| 5,250,058 * | 10/1993 | Miller et al. .......................... 606/154 |
| 5,366,462 * | 11/1994 | Kaster et al. ......................... 606/153 |
| 5,486,187 * | 11/1994 | Schenck ............................... 606/153 |
| 5,695,504 | 12/1997 | Gifford, III et al. . |

FOREIGN PATENT DOCUMENTS

| | | |
|---|---|---|
| 195 42 733 | 7/1997 | (DE) . |
| 0 820 724 | 1/1998 | (EP) . |

\* cited by examiner

*Primary Examiner*—Michael Buiz
*Assistant Examiner*—Lien Ngo
(74) *Attorney, Agent, or Firm*—Wenderoth, Lind & Ponack, L.L.P.

(57) ABSTRACT

The invention concerns a connecting device for anastomosis of a vascular prosthesis to a tubular conduit in which a lateral or terminal opening has been formed, the prosthesis including, at a connecting end, a turned-back portion forming an annular layer whose free edge is adapted to be pressed onto the immediate vicinity of the rim of the tubular conduit. The connecting device includes a set of fasteners each of which is adapted to press the annular layer onto the rim of the opening. It further includes an annular support along which the fasteners are distributed. The fitting device includes a connecting device and a releasable holding mechanism for holding the fasteners in the open position. The implant comprises a vascular prosthesis and a fitting device.

19 Claims, 6 Drawing Sheets

CONNECTING DEVICE FOR ANASTOMOSIS, DEVICE FOR FITTING FASTENERS AND IMPLANT INCLUDING THEM

The present invention concerns a connecting device for anastomosis of a tubular prosthesis to a tubular conduit in which a lateral or terminal opening has been formed, the prosthesis including, at a connecting end, a turned-back portion forming an annular layer whose free edge is adapted to be pressed onto the immediate vicinity of the rim of the opening in the tubular conduit.

It also concerns a device for fitting fasteners for anastomosis of a tubular prosthesis to a tubular conduit in which a lateral or terminal opening has been formed, the device including, at a connecting end, a turned-back portion forming an annular layer whose free edge is adapted to be pressed onto the immediate vicinity of the rim of the opening in the tubular conduit.

It finally concerns an implant comprising a tubular prosthesis, in particular a vascular prosthesis, and a device for fitting a set of fasteners.

The vascular prostheses routinely used at present are made by weaving or knitting fibers. They constitute substantially cylindrical conduits adapted to bypass or to be substituted for portions of diseased tubular conduits.

Anastomosis of a vascular prosthesis consists in causing it to communicate with a blood vessel, for example a vein or an artery. In particular, it consists in butt-jointing the prosthesis and the vessel.

An unhealthy portion of a vessel is replaced by termino-terminal anastomosis; in other words the prosthesis is axially aligned with the healthy part of the vessel, replacing a diseased portion that has been removed.

A bypass entails termino-lateral anastomosis; in other words the mouth of the prosthesis is connected laterally to the vessel, in which a lateral opening has previously been formed for this purpose.

In a first kind of anastomosis the prosthesis is sewn to the vessel using a suture. In this case, the vascular prosthesis and the blood vessel are sewn edge to edge.

In a second kind of anastomosis, the prosthesis has at the connection end an outwardly turned-back portion forming an annular layer whose free edge is adapted to be pressed onto the immediate vicinity of the rim of the opening formed in the blood vessel. In this case, the anastomosis of the vascular prosthesis to the blood vessel is effected by fitting a system of fasteners, also known as "clips", in order to clamp the annular layer to the rim of the opening in the blood vessel to attach it thereto.

To ensure a satisfactory connection, it is necessary to fit fasteners approximately every 4 mm around the rim of the opening. Each fastener is fitted individually, making the operation a lengthy one, which can be harmful to the health of the patient because circulation through the blood vessel must be interrupted while the prosthesis is being fitted.

French patent application FR-A-2 751 867 filed in the name of the Association René Leriche describes anastomosis of a vascular prosthesis to a blood vessel using the above method.

It is very difficult to fit each of the fasteners in succession without having to increase the size of the incision by the method described in the above document. Also, this technique is very time-consuming when used in the coele-surgery field.

SUMMARY OF THE INVENTION

The aim of the invention is to provide means for fast anastomosis between a tubular prosthesis, for example a vascular prosthesis, and a tubular organic conduit, for example a blood vessel, in particular in a limited operating field.

To this end, the invention consists in a connecting device for anastomosis of a tubular prosthesis to a tubular conduit in which a lateral or terminal opening has been formed, the prosthesis having, at a connecting end, a turned-back portion forming an annular layer whose free edge is adapted to be applied to the immediate vicinity of the rim of the opening in the tubular conduit. The connecting device includes a set of fasteners each adapted to press the annular layer onto the rim of the opening, and an annular support around which the fasteners are distributed.

In particular embodiments, the connecting device includes one or more of the following features:

said annular support is in one piece with the fasteners;

said annular support is removable to enable the set of fasteners to be separated;

said fasteners, which form clamps, include two jaws and each jaw is elastically deformable between a rest position in which the fastener is closed, the two jaws being in contact, and an open position enabling it to be fitted, in which the two jaws are spread apart;

in the closed position, the fasteners lie substantially along a generatrix of the annular support; and in the closed position, the fasteners are substantially radial relative to the annular support.

The invention also consists in a device for fitting fasteners for anastomosis of a tubular prosthesis to a tubular conduit in which a lateral or terminal opening has been formed, the prosthesis having, at a connecting end, a turned-back portion forming an annular layer whose free edge is adapted to be pressed onto the immediate vicinity of the rim of the opening in the tubular conduit. The device comprises a connecting device as defined above and means for releasably holding the set of fasteners in the open position.

In particular embodiments, the device includes one or more of the following features:

the an immobililizing mechanism releasable retaining mechechanism include, for each fastener, an immobilizing mechanism for immobilizing a first jaw relative to the annular support and a temporary immobilization mechanism for temporarily immobilizing the second jaw relative to the first jaw;

the temporary immobilizing mechanism includes a rigid outer ring for retaining the ends of the second jaws of each fastener;

the temporary immobilizing mechanism includes fragile ties providing the connection between the second jaws and the annular support;

the temporary immobilizing mechanism includes an inner sleeve for retaining the ends of the second jaws of each fastener, which sleeve slides relative to the annular support;

device includes a tubular support carrying the annular support at one end, which tubular support delimits a passage for receiving the tubular prosthesis, and the releasable retaining mechanism includes a remote releasing mechanism for remotely releasing the temporary immobilizing mechanism, which remote releasing mechanism is movable relative to the tubular support member;

the lengths of the tubular support member and the remote releasing mechanism are sufficient to enable them to be actuated manually from outside the body, the support and the remote releasing mechanism passing through an incision in the body;

the remote releasing mechanism includes a sleeve carrying the rigid outer ring at one end, which sleeve slides relative to the tubular support member to move said rigid ring away from the second jaws of each fastener;

the remote releasing mechanism includes at least one cutting member at the end of a sleeve which is movable relative to the tubular support member, the or each cutting member being adapted to cooperate with the fragile ties; and the remote releasing mechanism includes a sleeve extending the inner sleeve, which sleeve slides relative to the tubular support member to move the inner sleeve away from the second jaws of each fastener.

The invention equally consists in an implant including a tubular prosthesis, in particular a vascular prosthesis, having at a connecting end a turned-back portion forming an annular layer whose free edge is adapted to be pressed onto the immediate vicinity of the rim of the opening in a tubular conduit to which the tubular prosthesis is to be anastomized and a fastener-fitting device as defined above.

BRIEF DESCRIPTION OF THE DRAWINGS

The invention will be better understood after reading the following description which is given by way of example only and with reference to the drawings, in which.

DETAILED DESCRIPTION OF THE INVENTION

Figure 1:
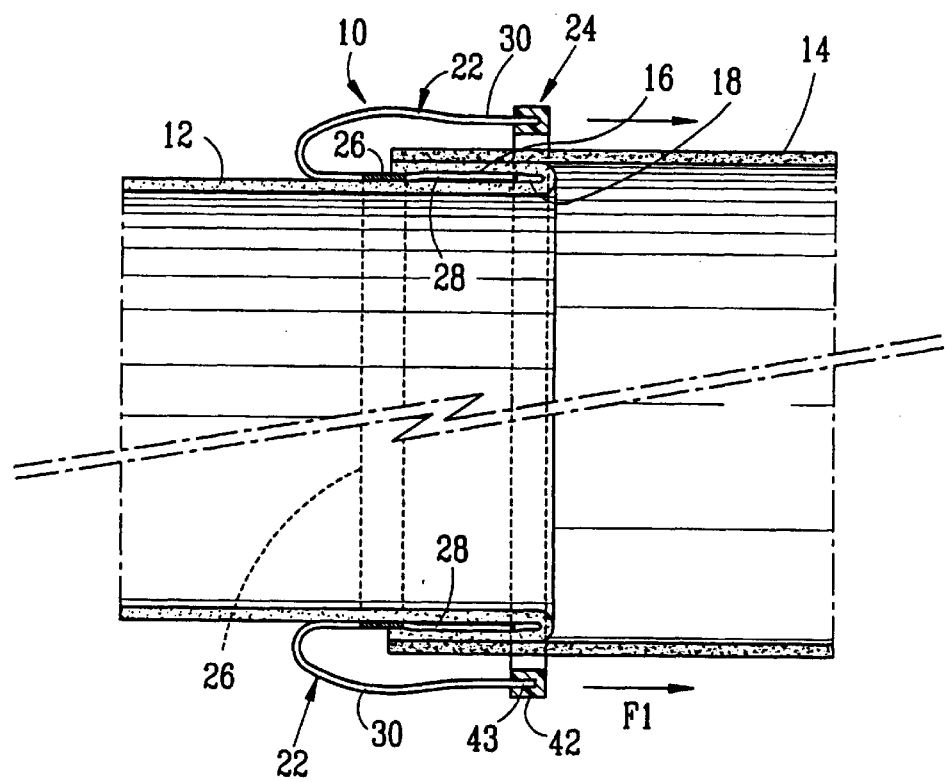
FIG. 1 is a sectional view of a device in accordance with the invention for fitting fasteners for termino-terminal anastomosis, the device being shown before the fasteners are released.

FIG. 1 shows a fastener-fitting device 10 for use in termino-terminal anastomosis of a vascular prosthesis 12 to a tubular conduit 14, for example an artery.

The prosthesis 12 has an annular external layer 16 at the end connected to the tubular conduit 14. It is formed by the end portion of the prosthesis which is folded back outwardly and constitutes a turned-back portion. The turned-back portion 16 defines a cylindrical layer externally surrounding the end of the prosthesis 12. In conjunction with the main part of the prosthesis 12, this layer therefore delimits an annular passage 18.

The fastener-fitting device 10 includes a connecting device 20 carrying the fasteners 22 and means 24 for releasably holding the set of fasteners in the open position.

Figure 2:
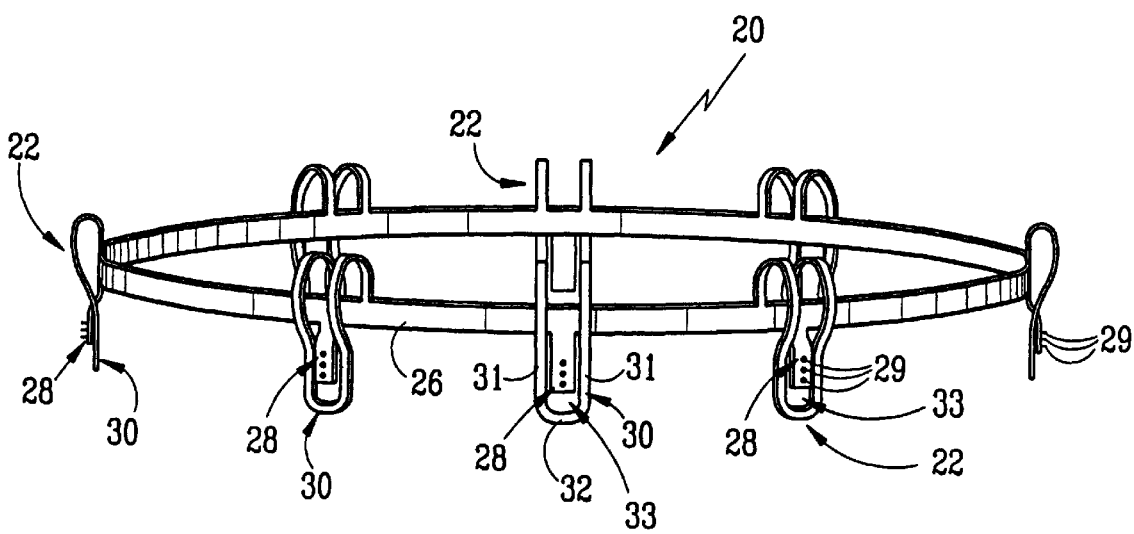
FIG. 2 is a perspective view of a connecting device in accordance with the invention used in the device from FIG. 1.

FIG. 2 shows the connecting device on its own and to a larger scale.

In this example, the connecting device includes eight fasteners 22 regularly distributed around the perimeter of a closed annular support 26. The annular support 26 is a metal ring with which the fasteners 22 are in one piece.

Each fastener 22 includes two jaws and forms a clamp. Each fastener is deformable elastically between a rest position (FIG. 2), which is the position in which it is made, with the two jaws in contact, and an open position enabling it to be fitted, in which the two jaws are spread apart.

Each fastener includes a first jaw 28 adapted to be received in the passage 18 defined between the main part of the prosthesis 12 and the turned-back portion 16. This first or inner jaw is a planer tongue substantially parallel to a generatrix of the annular support 26, with a slight outward offset. It advantageously has three retaining pips 29 on the surface intended to be pressed against the turned-back portion 16.

The second jaw 30, intended to be pressed elastically onto the outside surface of the tubular conduit 14, is arcuate and generally U-shaped. It is formed by two parallel branches 31 in one piece with the annular support 26, on the side thereof opposite that carrying the inner jaw 28. The two parallel branches 31 are joined together by a bridge 32 and thus delimit an opening 33 to receive the inner jaw 28.

The two main branches 31 are bent outwards in the manner of a hairclip towards and beyond the inner jaw 28. The distance between the two parallel main branches 31 is greater than the width of the inner jaw 28 and the jaw is therefore received between the two branches 31 when the fastener is in its rest position. The end of the second jaw 30 is flattened and lies in a plane parallel to that of the inner jaw 28.

Figure 3:
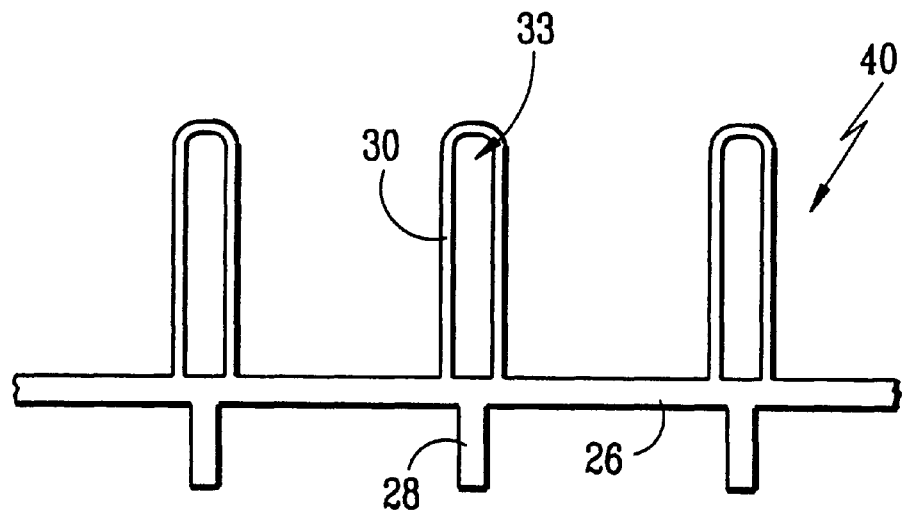
FIG. 3 is an elevation view of a portion of a blank cut out from a strip and used to make the connecting device from FIG. 2.
Figure 4:
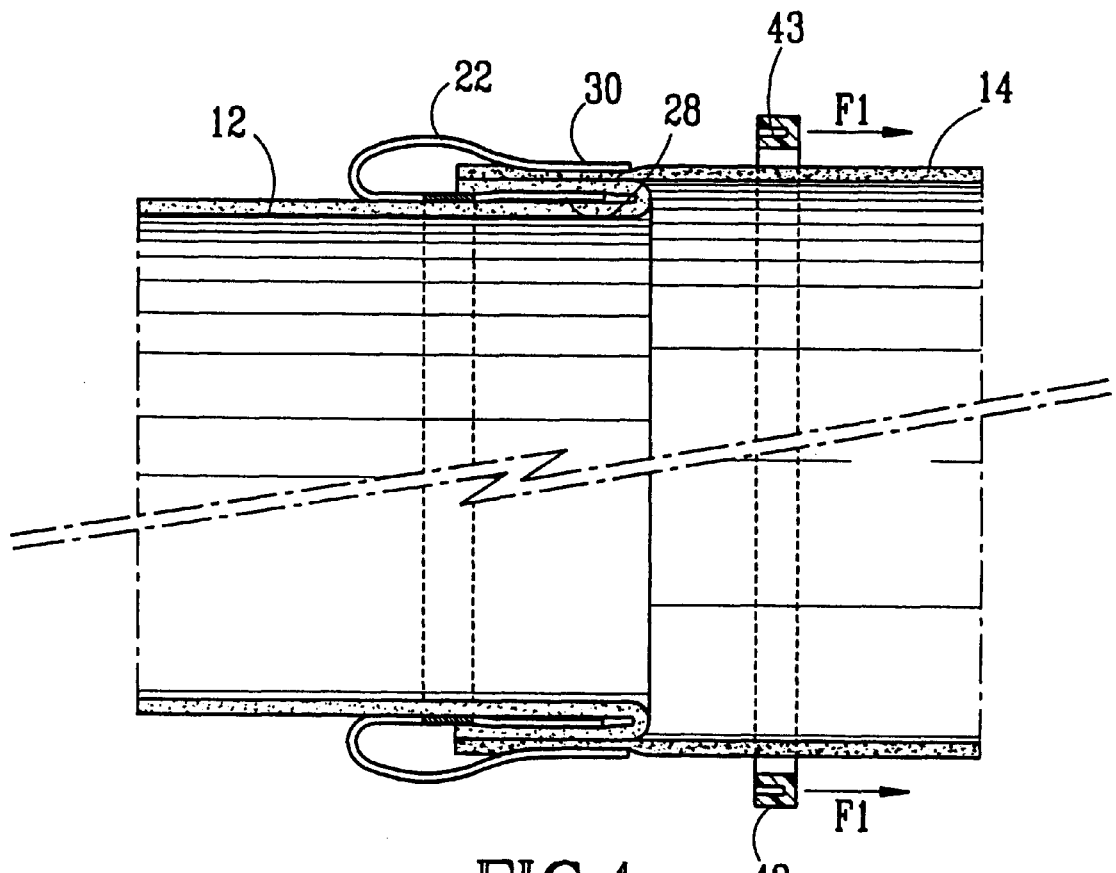
FIG. 4 is a view analogous to that of FIG. 1, after the fasteners are released.

FIG. 3 shows a portion of a blank 40 from which the connecting device shown in FIG. 2 is made. This blank is cut, for example stamped, from a flat metal strip.

The first jaws 28 and the second jaws 30 with the openings 33 in them to receive the first jaws are recognizable in FIG. 3.

To form the connecting device, the second jaws 30 are bent towards and beyond the first jaws 28 and in the process deform plastically. The support 26 is then configured into a circle and its two ends are welded edge to edge to form an annular ring. The whole of the connecting device is then heat-treated to impart the necessary elasticity to the fasteners.

As shown in FIG. 1, the means 24 for releasably holding the fasteners in the open position include means for temporarily immobilizing the second jaw 30 of each fastener relative to the first jaw 28, the first jaw 28 being itself immobilized by the annular support 26.

In the embodiment shown, the temporary immobilizing means include a ring 42 having an inside diameter greater than the outside diameter of the tubular conduit 14. The ring 42 is provided with blind holes 43 whose axes are parallel to the axis of the ring and which are intended to receive the planer ends of the second jaws 30.

The forces applied to the ring by the elastic second jaws cancel out because they are equal and converge at a common point. The ring 42 therefore holds the fasteners 22 in the open position and is held substantially on the axis of the annular support 26.

To perform the anastomosis of the prosthesis 12 to the end of the tubular portion 14, the inner jaws 28 of the fasteners are first inserted into the passage 18, as shown in FIG. 2. It is a simple matter to fit the connecting device between the main part of the prosthesis 12 and the turned-back portion 16 using the connecting device associated with a ring 24 for holding the fasteners in the open position.

The prosthesis 12 fitted in this way with the fastener-fitting device is then inserted into the end of the tubular conduit 14. In particular, the turned-back portion 16 is inserted into the tubular conduit 14 and the ring 42 and the second jaws 30 lie outside the end of the tubular conduit 14.

To join the prosthesis 12 to the end of the conduit 14, the ring 42 is moved on its own along the conduit 14 in the direction of the arrow F1.

As shown in FIG. 3, this displacement of the ring 42 releases the ends of the outer jaws 30. They then close onto the outside face of the tubular conduit 14, thus clamping the latter and the turned-back portion 16 between the two jaws of the fasteners.

The ring 42 is then removed, either by sliding it to the free end of the tubular portion 14 or by cutting it using an appropriate tool.

Figure 5:
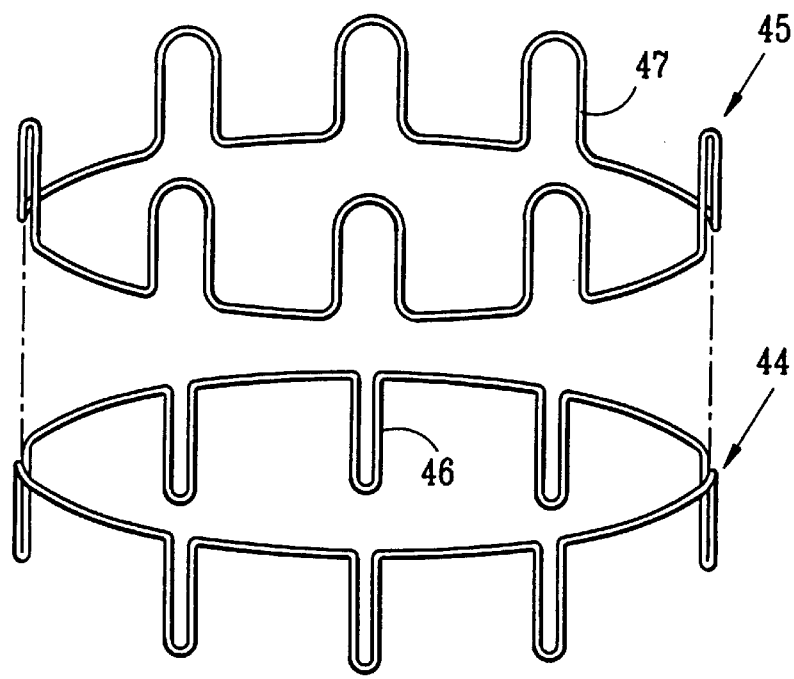
FIG. 5 is an exploded perspective view of one variant of a connecting device during fabrication.
Figure 6:
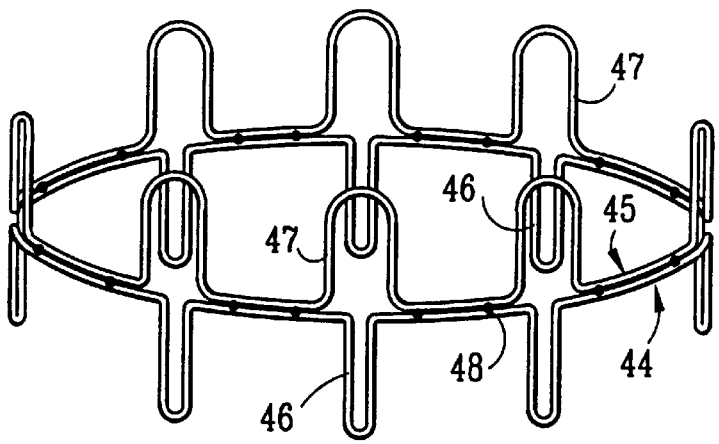
FIG. 6 is a perspective view of the connecting device from FIG. 5 during the next stage of its fabrication.
Figure 7:
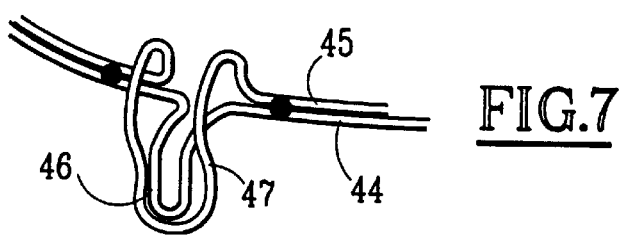
FIG. 7 is a partial perspective view of a finished fastener of the variant of the connecting device shown in FIGS. 5 and 6.

FIGS. 5 to 7 show a variant of the connecting device of the invention. In this embodiment, the device comprises two wires 44, 45 formed into rings with lobes 46, 47 each defining one jaw.

As shown in FIG. 6, the two wires 44, 45 are joined together by welds 48 with their associated lobes aligned with each other. The lobes 46, 47 are then deformed, as in the FIG. 2 embodiment, to define the elastic jaws of the fasteners. These can be seen in FIG. 7.

Figure 8:
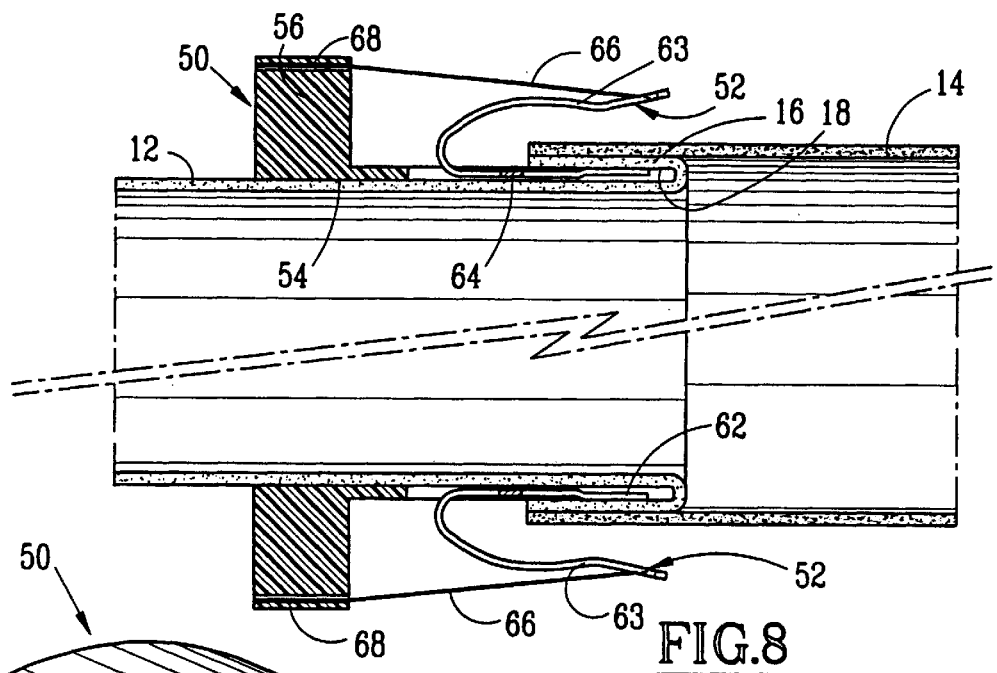
FIG. 8 is a sectional view of a variant of the fastener-fitting device from FIG. 1.

FIG. 8 shows a variant of the fastener fitting device. It includes a sleeve 50 forming an annular support over the periphery of which are distributed independent wire fasteners 52, eight of them in this example. The sleeve 50 has an inner cylindrical passage 54 whose diameter is slightly greater than the outside diameter of the prosthesis 12. It has an external peripheral flange 56 on its outside, at the rear. At the front, the sleeve 50 defines a thin bushing 58 adapted to be received in the passage 18 between the main part of the prosthesis 12 and the turned-back portion 16.

Figure 9:
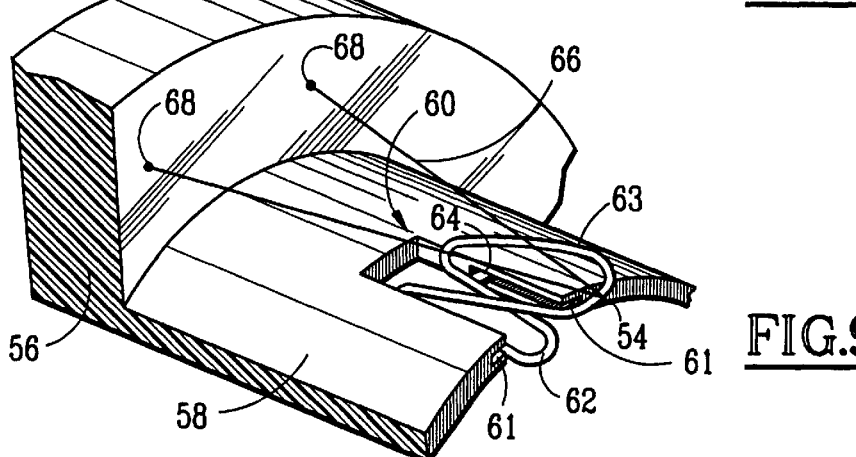
FIG. 9 is a partial perspective view of the fastener-fitting device shown in FIG. 8.

As shown in FIG. 9, the fasteners 52 are received in axial notches 60 regularly distributed on the bushing 58 and open at the front end of the sleeve. The notches 60 are substantially rectangular in shape and have axial grooves 61 for holding and guiding the fasteners 52 on their side wall, within the thickness of the bushing 58.

These fasteners have shapes analogous to those shown in FIGS. 2 and 7, in other words they include two jaws 62, 63 spring-loaded towards each other. However, they are not joined together by an annular support in one piece with them. On the other hand, lateral flanges 64 intended to be received in the slots 52 are provided on the fasteners on respective opposite sides of the connecting area between the two jaws 62, 63. The flanges 64 are formed by planer lugs of sufficient width to prevent the fasteners from rotating.

Accordingly, as shown in FIG. 9, the flanges 64 received in the grooves 61 retain and guide the fasteners 52 with their inner jaw aligned with the sleeve.

To hold each fastener 52 temporarily in the open position, its outer jaw 63 is held away from the inner jaw 62 by a fragile tie 66 passing through the fastener. This tie passes on either side through axial passages 68 in the flange 56.

Clearly, by virtue of its successive passages through the flange 56, a single tie 66 holds all the outer jaws of the fasteners carried by the sleeve in the spread-apart position.

The outer sleeve has an appropriate recessed profile, not shown, to facilitate passing the tie through it and retaining it at the end of the sleeve.

FIG. 8 shows that, to join the prosthesis 12 to the tubular conduit 14, the sleeve 50 carrying the fasteners 52 is placed around the prosthesis with the flange 58 and the inner jaw 62 of the fasteners in the passage 18. The ties 66 hold the outer jaws 63 in the spread-apart position and, before the tie 66 is cut, the jaws lie immediately above the outside surface of the tubular conduit 14.

Figure 10:
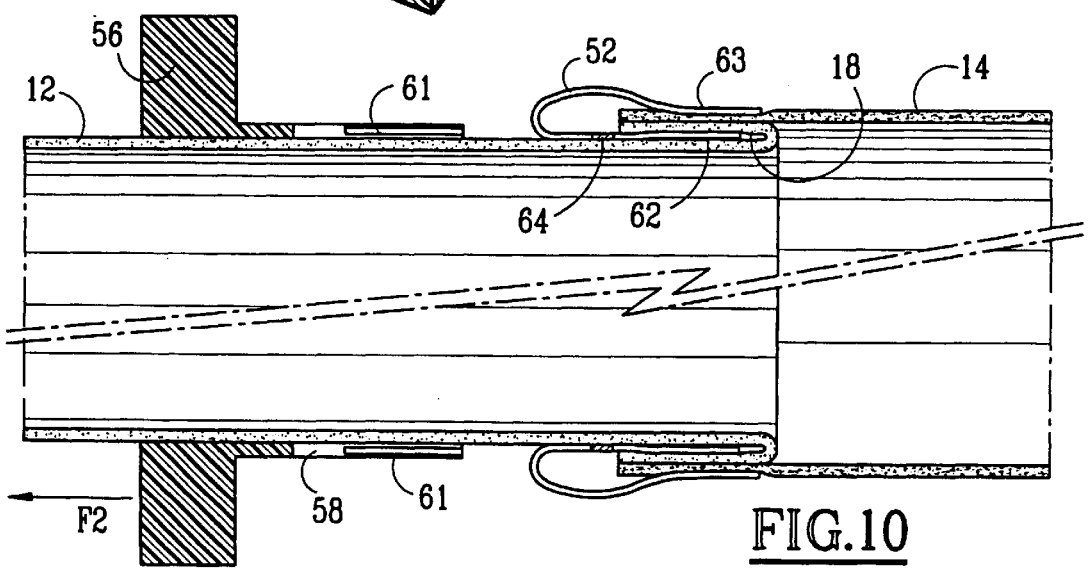
FIG. 10 is a sectional view showing the fastener-fitting device from FIGS. 8 and 9 after the fasteners are released.

When the tie is cut, the outer jaws 63 close up due to the inherent elasticity of each fastener and clamp the end of the conduit 14 and the turned-back portion 16. Finally, after the fasteners are released, the sleeve 50 is extracted by moving it along the prosthesis 12 in the direction of the arrow F2 (see FIG. 10). If necessary the sleeve 50 is cut to enable it to be removed.

In this embodiment, the fasteners are independent of each other after anastomosis has been carried out. The connecting area between the tubular conduit and the prosthesis is therefore free to expand radially, in particular when cardiac pulses temporarily increase the blood flowrate.

Figure 11:
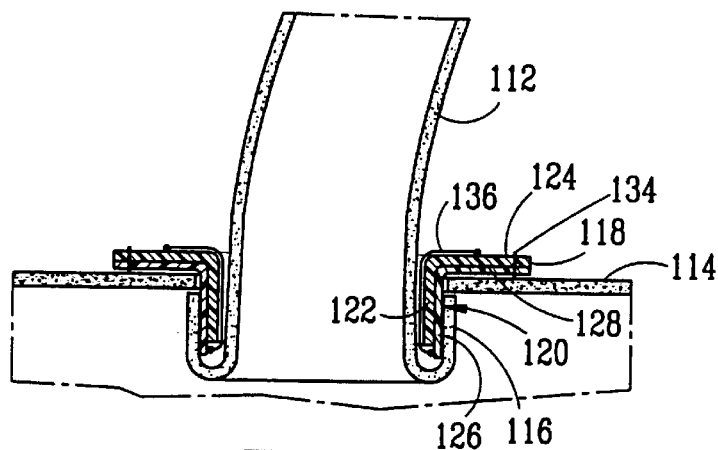
FIG. 11 is a sectional view of a fastener-fitting device in accordance with the invention for use in termino-lateral anastomosis, shown before the fasteners are released.

FIG. 11 shows a fastener-fitting device for use in termino-lateral anastomosis.

In this kind of anastomosis, the prosthesis 112 is designed to be attached to a tubular conduit 114 in which a substantially circular lateral opening has been formed. The prosthesis 112 has at its connecting end a turned-back portion 116 constituting a layer whose edge is intended to be pressed against the inside of the perimeter of the opening formed in the conduit 114.

For performing this kind of anastomosis, the fastener-fitting device includes an annular support 118 with elastic fasteners 120 at its periphery.

The support 118 is a rigid plastic ring with an L-shaped cross section. To be more precise, it includes a tubular portion 122 adapted to be engaged during fitting between the main part of the prosthesis 112 and the turned-back portion 116. It further includes an outer flange 124 aligned with the tubular section 122.

Figure 12:
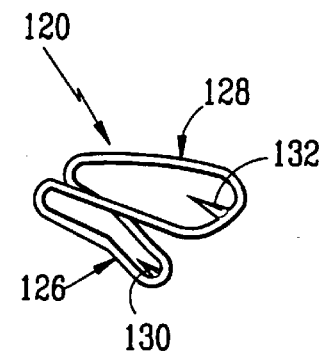
FIG. 12 is a perspective view of a fastener used in the device shown in FIG. 11.

The fasteners 120 are elastic clamps like that shown in FIG. 12, for example. They are formed from wire shaped into a closed ring and to define an inner jaw 126 and an outer jaw 128, as explained previously. The elasticity of the fastener is sufficient to enable an angular offset of the two jaws relative to each other a the order of 90° and to enable the two jaws to return to their rest positions, which are in substantially the same plane, when they are released.

Furthermore, the jaws 126, 128 each have a respective stud 130, 132 inside the turned-back portion at their end.

These are for ties for holding the fastener in the open position to pass through the circular lateral opening of the tubular conduit 114.

FIG. 11 shows how the fasteners are initially held in an open position in the acute angle between the tubular portion 122 and the flange 124.

To this end, a tie 134 passing axially through the flange 124 presses the outer jaw 128 of the fastener against the flange. The tie 134 passes around the stud 132 for this purpose.

Similarly, a tie 136 with one end engaged with the stud 130 extends along the inside cylindrical wall of the portion 122 and is fastened to the exposed face of the flange 124. Thus the fasteners are held in their open position against the annular support 118.

To fit the prosthesis, the inner jaw 126 of the fasteners, pressed against the tubular portion 122, is inserted into the passage between the main part of the prosthesis 112 and the turned-back portion 116. The resulting assembly constitutes a vascular implant that is advantageously marketed pre-assembled. The prosthesis, equipped in this way with the fastener-fitting device, is then inserted through the lateral opening formed in the conduit 114.

When the outer jaws of the fasteners are pressed onto the outer surface of the tubular conduit 114, the ties 136 are cut to release the inner jaws 126, which press the turned-back portion 116 against the inside surface of the conduit 114 because of the elasticity of the fasteners.

Figure 13:
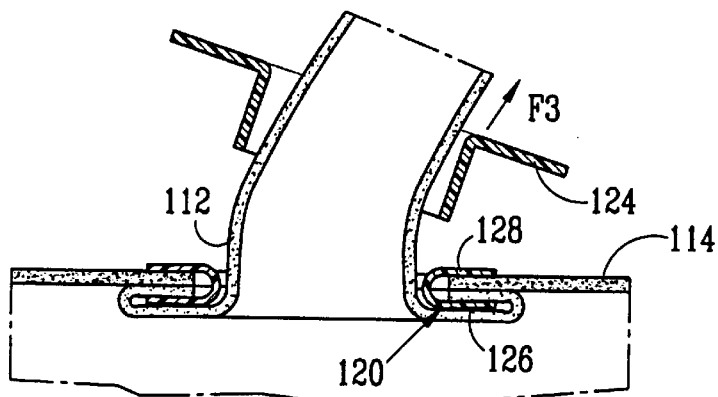
FIG. 13 is a view analogous to that of FIG. 11, showing the device after the fasteners are released.

The ties 134 are then cut to enable the ring 124 to be removed by sliding it in the direction of the arrow F3 (see FIG. 13).

Figure 14:
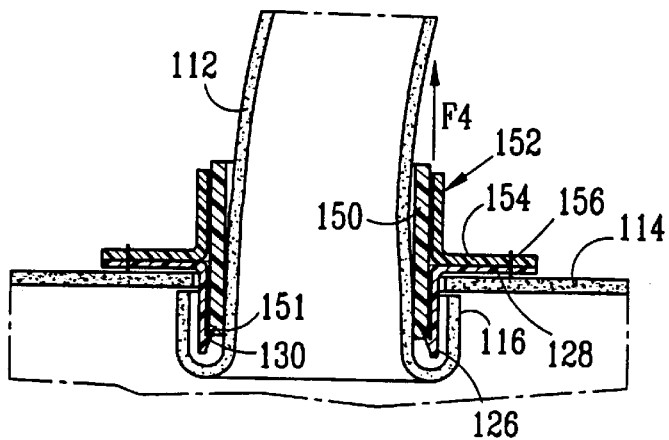
FIG. 14 is a sectional view of one variant of a fastener-fitting device for use in termino-lateral anastomosis.

FIG. 14 shows a further embodiment of the fastener-fitting device for termino-lateral anastomosis. The fasteners in this embodiment are similar to those of the embodiment shown in FIGS. 11 to 13.

The support for the fasteners is made up of two sliding parts. A first part, for holding the inner jaw 126, comprises a thin oval section sleeve 150. The sleeve has axial openings 151 within the thickness of one of its ends receiving the studs 130.

The second part 152 is a ring with an L-shaped section. The inside diameter of the ring is equal to the diameter of the sleeve 150 and the latter can therefore slide inside the ring 152.

The radial branch 154 of the ring 152 includes fragile ties 156 for retaining the outer jaw 128 of the fasteners.

The sleeve 150 and the inner jaw 126 are in the passage between the main part of the prosthesis and the turned-back portion 116. The end of the prosthesis is introduced into the lateral opening in the conduit 114 and the outer jaw is pressed onto the lateral outer surface of the conduit.

The sleeve 150 is then slid in the direction of the arrow F4 inside the ring 152. This displacement of the sleeve 150 releases the inner jaw 126 which then presses the turned-back portion 116 onto the inside surface of the conduit 114. The fragile ties 156 are then cut to release the fasteners and so that the ring 152 can be removed.

Figure 15:
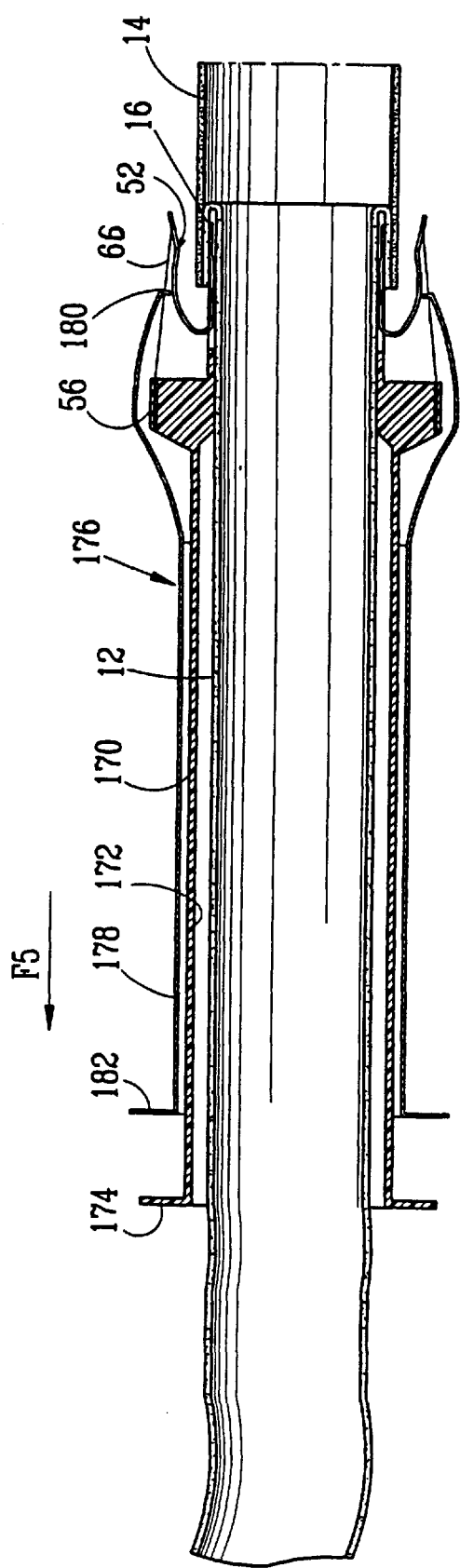
FIG. 15 is a view in longitudinal section of another variant of the fastener-fitting device from FIG. 1, including means for remote freeing of the fasteners.

FIG. 15 shows a variant of the fastener-fitting device from FIG. 8. Analogous parts are designated by the same reference numbers.

In this variant, the sleeve 50 is extended around the prosthesis 12 by a tubular extension 170 forming a support. This is advantageously a spring with contiguous turns. It defines a conduit 172 through which the main part of the prosthesis 12 passes. At its free end opposite the sleeve 50, the extension 170 has a flange 174 enabling it to be actuated manually. The length of the extension 170 is sufficient to enable the connecting device to be inserted in the body, the flange 174 remaining outside the body.

In this embodiment, the releasable means for retaining the fasteners in the open position include means 176 for remotely releasing the temporary immobilizing means 66 which here are in the form of fragile ties. The releasing means 176 include a tubular sleeve 178 which can slide axially on the outside of the tubular extension 170. The end of the sleeve 178 adjoining the fasteners carries cutting members 180 adapted to cooperate with the fragile ties 66. The cutting members are sharp blades pressed against the fragile ties 66, for example.

The sleeve 178 has a flange 182 at the other end for actuating it manually. The length of the sleeve 178 is sufficient to enable the releasing means 176 to be actuated from outside the body of the patient with the connecting device inside the body of the patient.

With a device of this kind, it is possible to release the fasteners 52 by simply pulling the sleeve 178 in the direction of the arrow F5, the tubular support 170 being held in a fixed position. This traction causes the releasing means 176 to slide relative to the extension 172. This sliding causes the cutting members 180 to rupture the fragile ties 166.

When the fasteners are released, the sleeve 50, which is fastened to the tubular support 170, and the release means 176 are extracted via the incision in the patient, only the prosthesis and the connecting device remaining in place.

The device shown in FIGS. 1 and 14 can also be provided with means for remotely releasing the temporary immobilizing means for the second jaws of the connecting device. To this end the rigid ring 42 or the sleeve 150 is fixed to the end of a rigid sleeve. The rigid arm slides on a tubular extension around the prosthesis which supports the connecting device and holds it in position.

The description given here concerns means for anastomosis of a vascular prosthesis to an artery or a vein. Nevertheless, these means can be used to join any type of tubular prosthesis to an organic tubular conduit such as the intestine or the ureter.

What is claimed is:

1. A connecting device for anastomosis of a tubular prosthesis to a tubular conduit in which a lateral or terminal opening is formed, the prosthesis having a connecting end comprising a turned-back portion forming an annular layer whose free edge is adapted to be applied adjacent a rim of the opening in the tubular conduit, said connecting device comprising:

a set of fasteners which form clamps adapted to press the annular layer of the prosthesis onto the rim of the opening of the tubular conduit; and an annular support around which said fasteners are distributed;

wherein each of said fasteners includes first and second jaws and is elastically deformable between a rest position in which said first and second jaws are in a closed, clamping position for clamping the annular layer of the prosthesis to the rim of the opening of the tubular conduit, and an open position in which said first and second jaws are spread apart to enable said fastener to be fitted to the annular layer of the prosthesis and the rim of the opening of the tubular conduit in preparation for clamping thereof.

2. A connecting device according to claim 1, wherein said annular support is in one piece with said fasteners.

3. A connecting device according to claim 1, wherein said annular support is removable from said fasteners to enable said fasteners to be separated from one another.

4. A connecting device according to claim 1, wherein, in said rest position, said fasteners lie substantially along a generatrix of said annular support.

5. A connecting device according to claim 1, wherein, in said rest position, said fasteners are substantially radial relative to said annular support.

6. An apparatus for anastomosis of a tubular prosthesis to a tubular conduit in which a lateral or terminal opening is formed, the prosthesis having a connecting end comprising a turned-back portion forming an annular layer whose free edge is adapted to be applied adjacent a rim of the opening in the tubular conduit, said apparatus comprising:

a connecting device comprising a set of fasteners which form clamps adapted to press the annular layer of the prosthesis onto the rim of the opening of the tubular conduit, and an annular support around which said fasteners are distributed, wherein each of said fasteners includes first and second jaws and is elastically deformable between a rest position in which said first and second jaws are in a closed, clamping position for clamping the annular layer of the prosthesis to the rim of the opening of the tubular conduit, and an open position in which said first and second jaws are spread apart to enable said fastener to be fitted to the annular layer of the prosthesis and the rim of the opening of the tubular conduit in preparation for clamping thereof; and a releasable retaining mechanism for releasably holding said fasteners of said connecting device in said open position.

7. An apparatus according to claim 6, wherein said releasable retaining mechanism includes, for each fastener, an immobilizing mechanism for immobilizing said first jaw relative to said annular support and a temporary immobilizing mechanism for temporarily immobilizing said second jaw relative to said first jaw.

8. An apparatus according to claim 1, wherein said temporary immobilizing mechanism includes a rigid outer ring for retaining an end of said second jaw of each of said fasteners.

9. An apparatus according to claim 7, wherein said temporary immobilizing mechanism includes fragile ties providing connection between said second jaws and said annular support.

10. An apparatus according to claim 7, wherein said temporary immobilizing mechanism includes an inner sleeve for retaining an end of said second jaw of each of said fasteners, said inner sleeve being slidable relative to said annular support.

11. An apparatus according to claim 7, further comprising a tubular support carrying said annular support at one end, said tubular support delimiting a passage for receiving the tubular prosthesis, and wherein said releasable retaining mechanism includes a remote releasing mechanism for remotely releasing said temporary immobilizing mechanism for temporarily immobilizing said second jaw, said remote releasing mechanism being movable relative to said tubular support member.

12. An apparatus according to claim 11, wherein said tubular support member and said remote releasing mechanism are sufficiently long to enable them to be actuated manually from outside a body having an incision through which said tubular support member and said remote releasing mechanism pass.

13. An apparatus according to claim 11, wherein said temporary immobilizing mechanism includes a sleeve carrying said rigid outer ring at one end, said sleeve being slidable relative to said tubular support to move said rigid ring away from said second jaw of each of said fasteners.

14. A device according to claim 12, wherein said temporary immobilizing mechanism includes fragile ties providing connection between said second jaws and said annular support, and said remote releasing mechanism includes at least one cutting member at an end of a sleeve which is movable relative to said tubular support, said at least one cutting member being adapted to cooperate with said fragile ties.

15. An apparatus according to claim 11, wherein said temporary immobilizing mechanism includes an inner sleeve for retaining an end of said second jaw of each of said fasteners, said inner sleeve being slidable relative to said annular support, and said remote releasing mechanism includes a sleeve extending from said inner sleeve, said sleeve being slidable relative to said tubular support to move said inner sleeve away from said second jaw of each of said fasteners.

16. An apparatus according to claim 12, wherein said temporary immobilizing mechanism includes a sleeve carrying said rigid outer ring at one end, said sleeve being slidable relative to said tubular support to move said rigid ring away from said second jaw of each of said fasteners.

17. A device according to claim 13, wherein said temporary immobilizing mechanism includes file ties providing connection between said second jaws and said annular support, and said remote releasing mechanism includes at least one cutting member at an end of a sleeve which is movable relative to said tubular support, said at least one cutting member being adapted to cooperate with said fragile ties.

18. An apparatus according to claim 12, wherein said temporary immobilizing mechanism includes an inner sleeve for retaining an end of said second jaw of each of said fasteners, said inner sleeve being slidable relative to said annular support, and said remote releasing mechanism includes a sleeve extending from said inner sleeve, said sleeve being slidable relative to said tubular support to move said inner sleeve away from said second jaw of each of said fasteners.

19. An implant including:

a tubular prosthesis, comprising a vascular prosthesis, for anastomosis with a tubular conduit in which a lateral or terminal opening is formed, said tubular prosthesis having a connecting end comprising a turned-back portion forming an annular layer whose free edge is adapted to be applied adjacent a rim of the opening in the tubular conduit;

a connecting device comprising a set of fasteners which form clamps adapted to press said annular layer of said tubular prosthesis onto the rim of the opening of the tubular conduit, and an annular support around which said fasteners are distributed, wherein each of said fasteners includes first and second jaws and is elastically deformable between a rest position in which said first and second jaws are in a closed, clamping position for clamping said annular layer of said tubular prosthesis to the rim of the opening of the tubular conduit, and an open position in which said first and second jaws are spread apart to enable said fastener to be fitted to said annular layer of said tubular prosthesis and the rim of the opening of the tubular conduit in preparation for clamping thereof; and a releasable retaining mechanism for releasably holding said fasteners of said connecting device in said open position.

* * * * *